(12) United States Patent
Senaratne et al.

(10) Patent No.: US 10,100,339 B2
(45) Date of Patent: Oct. 16, 2018

(54) METHOD OF OPERATION OF FERMENTATION OF GASEOUS SUBSTRATE COMPRISING HYDROGEN

(76) Inventors: Ryan Senaratne, Fayetteville, AR (US); Brandon Beard, Springdale, AR (US)

( * ) Notice: Subject to any disclaimer, the term of this patent is extended or adjusted under 35 U.S.C. 154(b) by 645 days.

(21) Appl. No.: 13/989,148

(22) PCT Filed: Nov. 14, 2011

(86) PCT No.: PCT/US2011/001902
§ 371 (c)(1),
(2), (4) Date: May 23, 2013

(87) PCT Pub. No.: WO2012/074545
PCT Pub. Date: Jun. 7, 2012

(65) Prior Publication Data
US 2013/0244300 A1 Sep. 19, 2013

Related U.S. Application Data (60) Provisional application No. 61/458,976, filed on Dec. 3, 2010.

(51) Int. Cl.
| | |
|---|---|
| C12P 7/06 | (2006.01) |
| C12M 1/107 | (2006.01) |
| C12M 1/00 | (2006.01) |
| C12M 1/06 | (2006.01) |
| C12M 1/34 | (2006.01) |

(52) U.S. Cl.
CPC .............. *C12P 7/065* (2013.01); *C12M 21/04* (2013.01); *C12M 21/12* (2013.01); *C12M 27/02* (2013.01); *C12M 29/04* (2013.01); *C12M 29/18* (2013.01); *C12M 41/34* (2013.01); *Y02E 50/17* (2013.01); *Y02E 60/324* (2013.01)

(58) Field of Classification Search
CPC ...... C12P 7/56; C12R 1/145; Y10S 435/8215; Y10S 435/842
See application file for complete search history.

(56) References Cited

U.S. PATENT DOCUMENTS

| | | |
|---|---|---|
| 4,351,905 A | 9/1982 | Clyde |
| 4,393,136 A | 7/1983 | Cheetham |
| 4,400,470 A | 8/1983 | Zeikus |
| 4,654,123 A | 3/1987 | Berg |
| 4,737,459 A | 4/1988 | Zeikus |
| 4,886,751 A | 12/1989 | Thorsson |
| 5,173,429 A | 12/1992 | Gaddy |
| 5,182,199 A | 1/1993 | Hartley |
| 5,593,886 A | 1/1997 | Gaddy |
| 5,807,722 A | 9/1998 | Gaddy |
| 5,821,111 A | 10/1998 | Gaddy |
| 6,136,577 A | 10/2000 | Gaddy |
| 6,340,581 B1 | 1/2002 | Gaddy |
| 6,919,488 B2 | 7/2005 | Melnichuk |
| 7,285,402 B2 | 10/2007 | Gaddy |
| 2012/0088282 A1 | 4/2012 | Gaddy |

FOREIGN PATENT DOCUMENTS

| | | |
|---|---|---|
| WO | WO 98/00558 | 1/1998 |
| WO | WO 00/68407 | 11/2000 |

OTHER PUBLICATIONS

Abrini, J., Naveau etc. Clostridium autoethanogenum, Spenov, an Anaerobic Bacterium That Produces Ethanol from Carbon-Monoxide, Archives of Microbiology, 1994, 161(4), 345-51.
Bahl, et al "Continuous Production of Acetone and Butonol by Clostridium acetoutylicum in a Two-Stage Phosphate Limited Chemostat" Appl. Microbiol. Biotechnol 09-96;46:176-182.
Bahl, et al. "Nutritional Factors Affecting the Ratio of Solvents Produced by Clostridium acetobutylicum" Appl. Environ. Microbiol. (07-86) 52(1):169-172.
Barik et al. "Biological Production of Alcohols from Coal through Indirect Liquefaction" Appl. Biochem. Biotechnol. Proc of the 9th Symp on Biotechnol. for Fuels (1988) 18:363.
Bredwell, M.D. Srivastava et al. "Reactor Design Issues for Synthesis-Gas Fermentations" Biotechnol Prog. (1999) 15, 834-844.
Bryant et al. "Buffering as a Means for Increasing Growth and Butanol Production by Clostridium acetobutylicum" J. Indust Microbiol (02-88) 3:45:55.
Byung Hong Kim, P.B et al. "Control of Carbon & Electron Flow in Clostridium acetobutylicum Fermentations: Utilization of Carbon Monoxide to Inhibit Hydrogen Production and to Enhance Butanol Yields;" Applied Environmental Microbiology; (1984) 48 (4), 764-770.
Chang, I.S. et al. "CO Fermentation of Eubacterium limosum KIST612" Journal of Microbiology and Biotechnology; (1998); 8(2); 134-140.
Chang, I.S. et al. "Formulation of Defined Media for Carbon monoxide Fermentation by Eubacterium limosum KIST612 and the growth Characteristics of the Bacterium" Journal of Bioscience and Bioengineering, (1999) 88 (6), 682-685.
Clarke et al "Nature and Significance of Oscillatory Behaviour during Solvent Productioin by Clostridium acetobuylicum in Continuous Culture" 1987 Biotec Bioengin 32:538-544.
Degraef et al. "The Steady-State Internal redox State (NADH/NAD) Reflects the External Redox State and is Correlated with Catabolic Adaptation in *Escherichia coli*" J. Bacteriol, (Apr. 1999)181(8): 2351-2357.
Diekert, G. et al. "Metabolism of Homoacetogens" Antonie Van Leeuwenhoek International Journal of General and Molecular Microbiology, (1994) 66(1-3), 2009-221.

(Continued)

*Primary Examiner* — Christopher R Tate
*Assistant Examiner* — Aaron J Kosar
(74) *Attorney, Agent, or Firm* — James P. Krueger (57) ABSTRACT

The present disclosure provides methods of gaseous substrate fermentation comprising: adding gaseous substrate into an aqueous medium in a bioreactor. The methods of the present disclosure comprise: measuring cell density; adjusting input of gaseous substrate to increase cell density; changing hydrogen uptake.

4 Claims, 1 Drawing Sheet

(56) References Cited

OTHER PUBLICATIONS

Ferras et al "Acetonobutylic Fermentation: Improvement of Performances by Coupling Continuous Fermentation and Ultrafiltration" Biotechnol. Bioengin (Jun. 1985) 28:523.

Girbal, L. et al. Regulation of Metabolic Shifts in Clostridium Acetobutylicum ATCC 824 FEMS Microbiology Reviews (1995) 17(3) 287-297.

Gottschal, J.C. et al. "The Induction of Acetone and Butanol Production in Cultures of Clostridium-Acetobutylicum by Elevated Concentrations of Acetate and Butyrate," FEMS Microbiology Letters (1981) 12 (4) 385-389.

Gottwald et al. "The Internal pH of Clostridium acetobutylicum and its Effect on the Shift from Acid to Solvent Formation" Arch. Microbiol (Oct. 1985) 143:42-46.

Grahame et al. "Substrate and Cofactor Reactivity of a Carbon Monoxide Dehydrogenase-Corrinoid Enzyme Complex: Stepwise Reduction of Iron-Sulfur and Corrinoid Centers, the Corrinoid CO2 +/1+ Redox Midpoint Potential, and Overall Synthesis of Acetyl-COA" Biochem, (Oct. 12, 1993) 32:10786-93.

Guedon et al. "Carbon and Electron Flow in Clostridium cellulolyticum Grown in Chemostat on Synthetic Medium" J. Bacteriol (May 1999) 181 (10): 3262-3269.

Hansen, J.B. "High Conversion of Synthesis Gas into Oxygenates" Studies in Surface Science and Catalysis (1997) 61, 457-67.

Hols et al. "Acetate utilization in Lactococcus Lactis Deficient in Dehydrogenase: A Rescue Pathway for Maintaining Redox Balance" J. Bacteriol (Sep. 1999) 181 (17): 5521.

Huseman et al. "Solventogenesis in Clostridium acetobutylicum Fermentations related to Carboxylic Acid and Proton Concnetrations" Biotechnol Bioengin (Sep. 1988) 32:843-52.

Ingram et al. "Expression of Different Levels of Ethanologenic Enzymes from Zymomonas mobilis in Recombinant Strains of Escherichia coli" Appl. Environ. Microbiol (Feb. 1988) 54(2): 397-404.

Jung, G.Y.et al. "Isolation and Chracterization Rhodpseudomonas palustris P4 which utilizes CO with the production of H2" Biotechnology Letters (1999) 21(6) 525-529.

Kim et al. "Redox Potential in Acetone-Butanol Fermentations" 9th Symposium on Biotechnology for Fuels and Chemicals, Boulder Co (May 1987).

Kim et al. "Electron Flow Shift in Clostridium acetobutylicum Fermentation by Electrochemically Introduced Reducing Equivalent" Biotechnol Lett (Feb. 1988) 10(2): 123-128.

Klasson et al, "Biological Production of Ethanol from Coal Synthesis Gas-Medium Development Studies" Appl. Biochem Biotechnol Proceedings fr Symposium on Biotechnology for Fuels and Chemicals (1993) 39:40:559.

Klasson, K.T. et al. "Kinetics of Light Limited Growth and Biological Hydrogen-Production from Carbon-Mnoxide and Water" Rhodospirillum-Rubrum Journal of Biotech (1993) 29 (1-2), 177-188.

Klasson, K.T. et al. "Bioconversion of Synthesis Gas into Liquid or Gaseous Fuels" Enzyme and Microbial Technology (1992) 14(8) 602-608.

Klasson, K.T. "Biological conversion of Coal and Coal-Derived Synthesis Gas" Fuel (1993) 72(12), 1673-1678.

Klier, K "Methanol Synthesis" Advances in Catalysis (1982) Advances in Catalysis 31.

Krasna, A.I. et al. "The Inhibition of Hydrogenase by Nitric Oxide" Proceedings of the National Academy of Sciences (1954) 40(4), 225-227.

Krasna, A.I. "Hydrogenase: Properties and Application" Enzyme and Microbial Technology (1979) 1(3), 165-172.

Kutzenok, A. et al. "Degenerative Processes in a Strain of Clostridium Butylicum" Journal of Bacteriology (1952) 64(6), 829-836.

Landuyt et al. "Transition from Acid Fermentation to Solvent Fermentation in a Continuous Dilution Culture of Clostridium Thermosaccharolyticum" Annals of NY Acdy of Sciences (12-2987), 473-478.

Lemon, B.J. et al. "Binding of Exogenously added Carbon Monoxide at the Active Site of the iron-only Hydrogenase (Cpl) from Clostridium pasteurianum," Biochemistry (1999) 38(40), 12969-12973.

Liou et al. "Clostridium *Carboxidivorans* sp. nov., a Solvent-Producing Clostridium Isolated from an Agricultural Settling Lagoon, and Reclassification of the Acetogen Clostridium Scatologenes Strain SL1 as Clostridium *Drakei* sp. nov." Int. J. Sys. Evol. (Sep. 2005) Microbiol 55:2085-2091.

Ljungdahl, L.G. "The Autotrophic Pathway of Acetate Synthesis in Acetogenic Bacteria" Annual Rev of Microbiology (1986) 40, 415-450.

Long, et al. "Sporulation of Clostridium acetobutylicum P262 in a Defined Medium" Appl. Environ. Microbiol (Apr. 1983) 45(4):1389-1393.

Lovitt et al. "Ethanol Production by Thermophilic Bacteria: Biochemical Basis for Ethanol and Hydrogen Tolerance in Clostridum thermohydrosulfuricum" J. Bacteriol (Jun. 1988) 170(6):2809.

Lynd et al. "Thermophilic Ethanol Production" Appl. Biochem Biotech (1991) 28/29:549.

Martin et al. "Effects of Acetic and Butyric Acids on Solvent Production by Clstridium acetobutylicum" Biotech, Lett (Feb. 1983) 5(20):89-94.

Meyer,CL et al "Increased Levels of ATP and NADH Are Associated with Increased Solvent Production in Continuous Cultures of Clostridium acetobutylicum" Applied Microbiology and Biotechnology, (1989) 30(5) 450-459.

Meyer, C.L. et al. "The Effect of CO on Growth and Product Formation in Batch Cultures of Clostridium acetobutylicum" Biotechnology Letters (1985) 7(1) 37-42.

Meyer, C.L. et al. Carbon Monoxide Gasing Leads to Alcohol Production and Butyrate Uptake without Acetone Formation in Continuous Cultures of Clostridium acetobutylicum Applied Microbiology and Biotechnology (1986) 24(2), 159-167.

Misoph, M. et al. "Effect of CO2 on the fermentation capacities of the acetogen Peptostreptococcus Productus U-1" Journal of Bacteriology (1996) 178(11) 3140-3145.

Murray et al "Ethanol Production by a Newly Isolated Anaerobe, Clostridium saccharolyticum: Effects of Culture Medium and Growth Condiditons" Canad J Microbiol (Mar. 1983) 29:342.

Philips et al. "Biological Production of Ethanol from Coal Synthesis Gas medium Development Studies" Appl Biochem Biotech, Proceedings from 14th Symposium on Biotechnology for Fuels and Chemicals (1990) 39/40:559.

Phillips et al. "Synthesis Gas as Substrate for the Biological Production of Fuels and Chemicals" Appl. Biochem. and Biotech, Proceedings of the 15th Symposium on Biotech for Fuels and Chemicals (1994) 45/46:145.

Ragsdale, S "Enzymology of the Acetyl-CoA Pathway of CO2 Fixation" Ctricical Reviews in Biochem and Mol Biology, (1991) 26, 261-300.

Ram et al. "Ethanol Production by Clostridium thermocellum SS8, A Newly Isolated Thermophilic Bacterium" Biotechnol Lett (Aug. 1989) 11(8):589-592.

Rao, et al. "Manipulation of End Product Distribution in Strict Anaerobes" Annals of NY Academy of Science (Nov. 1987) pp. 76-83.

Rao et al. "Altered Electron Flow in a Reducing Environment in Clostridium acetobutylicum" Biotech Lett (Feb. 1988)10(2):129-132.

Rao et al. "Directed Metabolic Flow with High Butane Yield and Selectivity in Continuous Culture of Clostridium acetobutylicum" Biotech Lett (May 1988) 10(5):313-318.

Rao, et al. "NADH Levels and Solventogenesis in Clostridium-Acetobutylicum-New Insights through Culture Fluorescence" Applied Microbiology & Biotech (1989) 30(1) 59-66.

Reardon et al. "Metabolic Pathway Rates and Culture Fluorescence in Batch Fermentations of Clostridium acetobutylicum" Biotech Prog (Sep. 1987) 3(3) 153-168.

Rothstein et al. "Clostridium thermosaccharolyticum Strain Deficient in Acetate Production" J. Baceriol (Jan. 1986) 165(1):319-320.

(56) References Cited

OTHER PUBLICATIONS

Terraciano et al. "Intracellular Conditions Required for Inititation of Solvent Production by clostridium acetobutylicum" Appl. and Environ. Microbiol. (Jul. 1986) 52(1): 86-91.

Taherzadeh et al. "The Effects of Pantothenate Deficiency and Acetate Addition on Anaerobic Batch Fermentation of Glucose by *Saccharomyces cerevisiae*" Appl. Microbiol. Biotech (Sep. 1996) 46:176-182.

Tibelius, K.H. et al. "Hydrogenase activity in Azospirillum brasilense is inhibited by nitrite, nitric oxide, carbon monoxide and acetylene," Journal of Bacteriology (1984) 160(1), 103-106.

Vasconcelos, I. et al. "Regulation of Carbon and Electron Flow in Clostridium Acetobutylicum Grown in Chemostat Culture at Neutral Ph on Mixtures of Glucose and Glycerol" Journal of Bacteriology; (1994) 176(5) 1443-1450.

Vega, J. L. et al. "The Biological Production of Ethanol from Synthesis Gas" Applied Biochemistry and Biotech (1989) 20-1, 781-797.

Vega, J. L. et al. "Design of bioreactors for coal synthesis gas fermentations" Resources, Conservation & Recycling (1990) 3(2-3) 149-160.

Vega et al. "The Biological Production of Ethanol from Synthesis Gas" Appl. Biochem. Biotechnol. Proc10th Symp on Biotechnol. for Fuels, Chemicals (1989) 20/21:781.

Wood, H.G., et al. "The Acetyl-CoA Pathway—A Newly Discovered Pathway of Autotrophic Growth" Trends in Biochemical Sciences (1986a); 11(1) 14-18.

Wood, H.G. et al. "The Acetyl-CoA Pathway of Autotrophic Growth" FEMS Microbiology Reviews (1986b) 39(4), 345-362.

Wood, H.G. et al. "A New Pathway of Autotrophic Growth Utilizing Carbon-Monoxide or Carbon-Dioxide and Hydrogen" (1986c) Biochemistry International 12(3), 421-440.

Worden, R.M. et al. "Engineering Issues in Synthesis-Gas Fermentations," 1997 American Chemical Society 18, 320-335.

Girbal, L. et al. "How Neutral Red Modified Carbon & Electron Flow in Clostridium acetobutylicum Grown in Chemostat Culture at Neutral pH" (1995)FEMS Micro. Review 16 151-162.

Kashket, E.R. et al. Clostridial strain degeneration, FEMS Microbiology Reviews (1995); 17(3), 307-315.

METHOD OF OPERATION OF FERMENTATION OF GASEOUS SUBSTRATE COMPRISING HYDROGEN

The present disclosure is generally directed to method of fermentation of a gaseous substrate comprising hydrogen. The present disclosure is specifically directed to method of fermentation of a gaseous substrate comprising hydrogen to produce one or more alcohols.

BACKGROUND

Methods for producing chemicals such as organic acids, e.g. acetic acid and alcohols, e.g. ethanol from microbial fermentation of gaseous substrates comprising carbon monoxide and hydrogen in media containing suitable nutrients and trace minerals using certain microorganism, such as those from the genus *Clostridium*, have been demonstrated. For example, U.S. Pat. No. 5,173,429 to Gaddy et al. discloses *Clostridium ljungdahlii* ATCC No. 49587, an anaerobic microorganism that produces ethanol and acetate from synthesis gas. U.S. Pat. No. 5,807,722 to Gaddy et al. discloses a method and apparatus for converting waste gases into useful products such as organic acids and alcohols using anaerobic bacteria, such as *Clostridium ljungdahlii* ATCC No. 55380. U.S. Pat. No. 6,136,577 to Gaddy et al. discloses a method and apparatus for converting waste gases into useful products such as organic acids and alcohols (particularly ethanol) using anaerobic bacteria, such as *Clostridium ljungdahlii* ATCC Nos. 55988 and 55989.

US Patent Application No. 20070275447 discloses a *clostridium* bacterial species (*Clostridium carboxidivorans*, ATCC BAA-624, "P7") that is capable of synthesizing, from waste gases, products which are useful as biofuel. U.S. Pat. No. 7,704,723 discloses a *clostridium* bacterial species (*Clostridium ragsdalei*, ATCC BAA-622, "P11") that is capable of synthesizing, from waste gases, products which are useful as biofuel.

WO 2007/117157 discloses use of *Clostridium autoethanogenum* (Accession No. DSM 10061, DSMZ, Germany) for the production of ethanol by anaerobic fermentation of substrates containing carbon monoxide. WO 2009/064200 discloses another bacteria (*Clostridium autoethanogenum*, Accession No. DSM 19630, DSMZ, Germany) for the production of ethanol by anaerobic fermentation of substrates containing carbon monoxide.

As described in the art, rate of production of chemicals such as alcohol depend on density of microbial cells ("cell density") in the fermentation medium. Adequately high cell density in the bioreactor is required in order to attain and maintain a high rate of production of chemicals.

U.S. Pat. No. 6,136,577 to Gaddy discloses a process of ethanol production in a fermentation process wherein cell-recycle is used to increase cell density.

U.S. Pat. No. 7,285,402 to Gaddy et al. discloses an anaerobic microbial fermentation process for the production of alcohol wherein a method of increasing cell density is presented during start up using a stock culture wherein there was excess $H_2$ present.

Start-up using a batch inoculum from stock culture ensures a healthy inoculum free from contaminants, but is not always successful as an inoculation procedure because of the rather low cell density employed, especially if the method parameters such as gas rate and agitation rate are pushed upward too rapidly just after inoculation.

Currently, there is a need in the art for improved methods to increase cell density in microbial fermentation of a gaseous substrate. The present disclosure provides a method to increase cell density at a faster rate for microbial fermentation methods of a gaseous substrate.

SUMMARY

The present disclosure provides a process of producing one or more alcohols from a gaseous substrate, comprising: fermenting a gaseous substrate comprising one or more of hydrogen ($H_2$) and carbon monoxide (CO) into an aqueous medium in a bioreactor; said process comprising increasing the cell density by adjusting hydrogen uptake; wherein adjusting hydrogen uptake comprises measuring rate of input of hydrogen; measuring rate of output of hydrogen; and adjusting rate of input of one or more of gaseous substrate and hydrogen; wherein adjusting hydrogen uptake comprises supplying said gaseous substrate such that molar ratio of said hydrogen uptake to rate of input of gaseous substrate comprises a first preselected range; wherein adjusting hydrogen uptake comprises supplying said gaseous substrate such that molar ratio of said hydrogen uptake to rate of input of hydrogen comprises a second preselected range; wherein the said first preselected range comprises a range of about 0.001 to about 1.0; wherein the said first preselected range comprises a range of about 0.005 to about 0.5; wherein the said second preselected range comprises a range of about 0.01 to about 0.1; wherein the said second preselected range comprises a range of about 0.001 to about 1.0; wherein the said second preselected range comprise a range of about 0.005 to about 0.5; wherein the said second preselected range comprise a range of about 0.01 to about 0.1; further comprising adding a flow of aqueous medium into the bioreactor; removing a flow of fermentation broth from the bioreactor; further comprising adding continuous flow of aqueous medium into bioreactor; removing a continuous flow of fermentation broth from the bioreactor; further comprising increasing the cell density by controlling rate of change of specific CO uptake; wherein controlling rate of change of specific CO uptake comprises measuring rate of input of CO; measuring rate of output of CO; measuring cell mass; and adjusting rate of input of CO; wherein rate of change of specific CO uptake comprises predetermined steps of specific CO uptake; wherein the said predetermined steps of specific CO uptake comprise a range of about 0.001 to about 10.0 mmol/min/gram thy cell; wherein the said predetermined steps of specific CO uptake comprise a range of about 0.01 to about 5.0 mmol/min/gram dry cell; wherein the said predetermined steps of specific CO uptake comprise a range of about 0.1 to about 1.0 mmol/min/gram dry cell; wherein said aqueous medium comprises one or more of the microorganism including: biologically pure microorganism, naturally occurring microorganism, non-naturally occurring microorganism, non-naturally occurring microorganism produced by genetic modification, mutant of naturally occurring microorganism, mutant of non-naturally occurring microorganism, recombinant microorganism, engineered microorganism, artificially synthesized microorganism; wherein said bioreactor comprises one or more reactor; wherein said bioreactor comprises cell recycle unit; wherein said CO-containing substrate comprises hydrogen; further comprising adding nutrient medium to said bioreactor.

The present disclosure provides: a method of gaseous substrate fermentation comprising: adding gaseous substrate comprising one or more of hydrogen ($H_2$) and carbon monoxide (CO) into an aqueous medium in a bioreactor; said aqueous medium comprising one or more microorganism; said method comprising increasing the cell density by adjusting hydrogen uptake; wherein adjusting hydrogen uptake comprises measuring rate of input of hydrogen; measuring rate of output of hydrogen; and adjusting rate of input of one or more gaseous substrate and hydrogen; wherein adjusting hydrogen uptake comprises supplying said gaseous substrate such that molar ratio of said hydrogen uptake to rate of input of gaseous substrate comprises a first preselected range.

As embodiments of the present disclosure: adjusting hydrogen uptake comprises supplying said gaseous substrate such that molar ratio of said hydrogen uptake to rate of input of hydrogen comprises a second preselected range; wherein the said first preselected range comprises a range of about 0.001 to about 1.0.

As embodiments of the present disclosure: the said first preselected range comprises a range of about 0.005 to about 0.5; wherein the said second preselected range comprises a range of about 0.01 to about 0.1; wherein the said second preselected range comprises a range of about 0.001 to about 1.0; wherein the said second preselected range comprise a range of about 0.005 to about 0.5; wherein the said second preselected range comprise a range of about 0.01 to about 0.1.

As an embodiment of the present disclosure, adding a flow of aqueous medium into the bioreactor; removing a flow of fermentation broth from the bioreactor. As an embodiment, adding continuous flow of aqueous medium into bioreactor; removing a continuous flow of fermentation broth from the bioreactor.

As embodiments of the present disclosure: increasing the cell density by controlling rate of change of specific CO uptake; wherein controlling rate of change of specific CO uptake comprises measuring rate of input of CO; measuring rate of output of CO; measuring cell mass; and adjusting rate of input of CO; wherein rate of change of specific CO uptake comprises predetermined steps of specific CO uptake; wherein the said predetermined steps of specific CO uptake comprise a range of about 0.001 to about 10.0 mmol/min/gram dry cell; wherein the said predetermined steps of specific CO uptake comprise a range of about 0.01 to about 5.0 mmol/min/gram dry cell; wherein the said predetermined steps of specific CO uptake comprise a range of about 0.1 to about 1.0 mmol/min/gram dry cell.

As an embodiment, said microorganism of the present disclosure comprises one or more of the microorganism including: biologically pure microorganism, naturally occurring microorganism, non-naturally occurring microorganism, non-naturally occurring microorganism produced by genetic modification, mutant of naturally occurring microorganism, mutant of non-naturally occurring microorganism, recombinant microorganism, engineered microorganism, and artificially synthesized microorganism; wherein said microorganism comprises selection from *Acetogenium kivui, Acetobacterium woodii, Acetoanaerobium noterae, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium autoethanogenum* (DSM 23693), *Clostridium autoethanogenum* (DSM 19630 of DSMZ Germany), *Clostridium autoethanogenum* (DSM 10061 of DSMZ Germany), *Clostridium thermoaceticum, Eubacterium limosum, Clostridium ljundahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium ultunense, Clostridium ragsdali* P11 (ATCC BAA-622), *Alkalibaculum bacchi* CP11 (ATCC BAA-1772), *Clostridium coskatii, Clostridium carboxidivorans* P7 (ATCC PTA-7827), *Geobacter sulfurreducens, Morrella thermacetica, Peptostreptococcus productus, Clostridium drakei,* recombinant microorganism (DSM 24138), and mixtures thereof; wherein said microorganism comprises one or more strains of *Clostridium ljundahlii,* or one or more strains of *Clostridium ragsdalei,* or one or more strains of *Clostridium carboxidivorans,* or one or more strains of *Clostridium autoethanogenum*; wherein said microorganism comprises one or more genetically modified microorganism produced by inserting one or more selected genes into host organism selected from any *Clostridium ljundahlii* strains, or any *Clostridium ragsdalei* strains, or any *Clostridium carboxidivorans* strains, or any *Clostridium autoethanogenum* strains; wherein said microorganism comprises one or more genetically modified microorganism produced by inserting into any host organism one or more genes from any *Clostridium ljundahlii* strain, or any *Clostridium ragsdalei* strain, or any *Clostridium carboxidivorans* strain, or any *Clostridium autoethanogenum* strain.

As embodiments of the present disclosure: said bioreactor comprises one or more reactor; wherein said bioreactor comprises cell recycle unit.

As an embodiment of the present disclosure, said CO-containing substrate comprises hydrogen.

As an embodiment of the present disclosure, the method comprises adding nutrient medium to said bioreactor.

DEFINITIONS

Unless otherwise defined, the following terms as used throughout this specification for the present disclosure are defined as follows and can include either the singular or plural forms of definitions below defined:

The term "about" modifying any amount refers to the variation in that amount encountered in real world conditions of sustaining microorganism culture, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about."

The term "acetogen" or "acetogenic" refers to a bacterium that generates acetate as a product of anaerobic respiration. These organisms are also referred to as acetogenic bacteria, since all known acetogens are bacteria. Acetogens are found in a variety of habitats, generally those that are anaerobic (lack oxygen). Acetogens can use a variety of compounds as sources of energy and carbon; the best studied form of acetogenic metabolism can use of carbon dioxide as a carbon source and hydrogen as an energy source.

The terms "bioreactor," "reactor," or "fermentation bioreactor," include a fermentation device consisting of one or more vessels and/or towers or piping arrangement, which includes the Continuous Stirred Tank Reactor (CSTR), Bubble Column, Gas lift Fermenter, Static Mixer, or other device suitable for gas-liquid contact. For the method of this disclosure, the fermentation bioreactor may comprise a growth reactor which feeds the fermentation broth to a second fermentation bioreactor, in which most of the product, ethanol, is produced.

The term "cell density" means mass of microorganism cells per unit volume of fermentation broth, e.g. g/liter.

The term "cell recycle" or "cell recycle system" or "crs" or "CRS" means arrangement of separating liquid (permeate) from solid microorganism cells in a fermentation broth and returning all or part of said separated solid microorganism cells back to fermentor that produced said fermentation broth using said microorganism. Generally a filtration device is used to accomplish said separation. A stream of solid microorganism free permeate stream and a stream of concentrated solid microorganism is produced from the filtration device. The solid free permeate stream may contain solid particles less than a specified particle size.

The term "conversion" means a fraction of input quantity that is converted into product(s); this is denoted in the following equation: (input quantity−output quantity)/(input quantity).

The term "ethanol productivity" means amount of ethanol produced per unit fermentor volume per day. The fermentor volume is effective volume or liquid volume in the fermentor.

The term "fermentation" means fermentation of CO to alcohols and acetate. A number of microorganism are known to be capable of carrying out the fermentation of CO to alcohols, including butanol and ethanol, and acetic acid, and are suitable for use in the process of the present disclosure. Examples of such microorganism that are suitable for use in the disclosure include those of the genus *Clostridium*, such as strains of *Clostridium ljungdahlii*, including those described in WO 2000/68407, EP 117309, U.S. Pat. Nos. 5,173,429, 5,593,886, and 6,368,819, WO 1998/00558 and WO 2002/08438, strains of *Clostridium autoethanogenum* (DSM 10061 and DSM 19630 of DSMZ, Germany) including those described in WO 2007/117157 & WO 2009/151342 and *Clostridium ragsdalei* (P11, ATCC BAA-622) including those described respectively in U.S. Pat. No. 7,704,723 and "Biofuels and Bioproducts from Biomass-Generated Synthesis Gas," Hasan Atiyeh, presented in Oklahoma EPSCoR Annual State Conference, Apr. 29, 2010 and *Clostridium* carboxidivorans (ATCC BAA-624) described in US Patent Application No. 20070275447. Other suitable microorganism include those of the genus *Moorella*, including *Moorella* sp HUC22-1, and those of the genus *Carboxydothermus*. The disclosures of each of these publications are fully incorporated herein by reference. In addition, other microorganism may be selected for use in the process of the disclosure by a person of skill in the art. It will also be appreciated that a mixed culture of two or more microorganism may be used in the process of the present disclosure. One microorganism suitable for use in the present disclosure is *Clostridium autoethanogenum*. Fermentation may be carried out in any suitable bioreactor, such as a continuous stirred tank reactor (CTSR), a bubble column reactor (BCR) or a trickle bed reactor (TBR). Also, in some preferred embodiments of the disclosure, the bioreactor may comprise a first, growth reactor in which the microorganisms are cultured, and a second, fermentation reactor, to which fermentation broth from the growth reactor is fed and in which most of the fermentation product (ethanol and acetate) is produced.

The term "fermentation broth" means: the composition of the fermentation medium comprises anything that ends up in the fermentation broth including: raw substrates, fermentation products, microorganism(s) and derived components, chemical additives, nutrients, gases. All three main phases; solid, liquid and gases are present in the fermentation broth and their possible interactions.

The term "gene" means a segment of DNA; it may include regions preceding and following the coding DNA as well as introns between the exons; may be a unit of heredity; In this disclosure the term "gene" includes a DNA segment that contributes to phenotype/function; the segments of DNA which cells transcribe into RNA and translate, at least in part, into proteins; a sequence (a string) of bases made up of combinations of A, T, C, and G. Generally, as provided in this disclosure, the definition can refer to either singular or plural meanings.

The term "microorganism" or "microbe" includes microorganism, fungi, yeast, archaea, and protists; microscopic plants (called green algae); and animals such as plankton, the planarian and the amoeba. Some also include viruses, but others consider these as non-living. Microorganisms live in all parts of the biosphere where there is liquid water, including soil, hot springs, on the ocean floor, high in the atmosphere and deep inside rocks within the Earth's crust. Microorganisms are critical to nutrient recycling in ecosystems as they act as decomposers. Microbes are also exploited by people in biotechnology, both in traditional food and beverage preparation, and in modern technologies based on genetic engineering. It is envisioned that mixed strain microorganisms, that may or may not contain strains of various microorganisms, will be utilized in the present disclosure. Also, it is envisioned that directed evolution can selectively screen microorganisms that can be utilized in the present disclosure. Also, it is envisioned that by mutagenesis of strains of existing microorganisms by treating them with various chemicals (to modify their DNA) can create microorganisms with superior performance. It is further envisioned that recombinant DNA technology can create microorganisms using select strains of existing microorganisms. It is envisioned that microorganism which are able to convert CO and water or $H_2$ and $CO_2$ into ethanol and acetic acid products will be utilized in the present disclosure. Some examples of useful microorganisms include *Acetogenium kivui, Acetobacterium woodii, Acetoanaerobium noterae, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium autoethanogenum* (DSM 23693), *Clostridium autoethanogenum* (DSM 19630 of DSMZ Germany), *Clostridium autoethanogenum* (DSM 10061 of DSMZ Germany), *Clostridium thermoaceticum, Eubacterium limosum, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium ultunense, Clostridium ragsdali* P11 (ATCC BAA-622), *Alkalibaculum bacchi* CP11 (ATCC BAA-1772), *Clostridium coskatii, Clostridium carboxidivorans* P7 (ATCC PTA-7827), *Geobacter sulfurreducens, Morrella thermacetica, Peptostreptococcus productus, Clostridium drakei*, recombinant microorganism (DSM 24138), and mixtures thereof. Other microorganism may be selected for use in these methods by one of skill in the art. Generally, as provided in this disclosure, the definition can refer to either singular or plural meanings.

The term "nutrient medium" comprises microorganism growth medium which may contain one or more of vitamins and minerals that permit growth of selected microorganism. Components of a variety of nutrient media suitable to the use of this invention are known and reported in prior publications such as International Patent Application No. WO 2008/00558, U.S. Pat. No. 7,285,402, U.S. Pat. No. 5,807,722; U.S. Pat. No. 5,593,886, and U.S. Pat. No. 5,821,111.

The term "specific CO uptake" means amount of CO in m-moles consumed by unit mass of microorganism cells (g) per unit time in min, i.e. m-mole/g/min.

The term "substrate" means a substance that is acted upon by an enzyme or microorganism to produce fermentation product. For example, sugar in sugar fermentation by enzymes to produce ethanol, one or more of CO, CO2 and $H_2$ in syngas fermentation by microorganism to produce one or more of carboxylic acid and alcohol.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is also used as intermediate in producing synthetic petroleum for use as a fuel or lubricant via Fischer-Tropsch synthesis and previously the Mobil methanol to gasoline process. Syngas consists primarily of hydrogen, carbon monoxide, and very often some carbon dioxide.

DETAILED DESCRIPTION

The present disclosure provides: a method of gaseous substrate fermentation comprising: adding gaseous substrate comprising one or more of hydrogen ($H_2$) and carbon monoxide (CO) into an aqueous medium in a bioreactor; said aqueous medium comprising one or more microorganism; said method comprising increasing the cell density by adjusting hydrogen uptake; wherein adjusting hydrogen uptake comprises measuring rate of input of hydrogen; measuring rate of output of hydrogen; and adjusting rate of input of one or more of gaseous substrate and hydrogen; wherein adjusting hydrogen uptake comprises supplying said gaseous substrate such that molar ratio of said hydrogen uptake to rate of input of gaseous substrate comprises a first preselected range.

As embodiments of the present disclosure: adjusting hydrogen uptake comprises supplying said gaseous substrate such that molar ratio of said hydrogen uptake to rate of input of hydrogen comprises a second preselected range; wherein the said first preselected range comprises a range of about 0.001 to about 1.0.

As embodiments of the present disclosure: the said first preselected range comprises a range of about 0.005 to about 0.5; wherein the said second preselected range comprises a range of about 0.01 to about 0.1; wherein the said second preselected range comprises a range of about 0.001 to about 1.0; wherein the said second preselected range comprise a range of about 0.005 to about 0.5; wherein the said second preselected range comprise a range of about 0.01 to about 0.1.

As an embodiment of the present disclosure, adding a flow of aqueous medium into the bioreactor; removing a flow of fermentation broth from the bioreactor. As an embodiment, adding continuous flow of aqueous medium into bioreactor; removing a continuous flow of fermentation broth from the bioreactor.

As embodiments of the present disclosure: increasing the cell density by controlling rate of change of specific CO uptake; wherein controlling rate of change of specific CO uptake comprises measuring rate of input of CO; measuring rate of output of CO; measuring cell mass; and adjusting rate of input of CO; wherein rate of change of specific CO uptake comprises predetermined steps of specific CO uptake; wherein the said predetermined steps of specific CO uptake comprise a range of about 0.001 to about 10.0 mmol/min/gram dry cell; wherein the said predetermined steps of specific CO uptake comprise a range of about 0.01 to about 5.0 mmol/min/gram dry cell; wherein the said predetermined steps of specific CO uptake comprise a range of about 0.1 to about 1.0 mmol/min/gram dry cell.

The present disclosure provides a continuous method of producing an alcohol product mixture comprising: adding gaseous substrate comprising carbon monoxide into an aqueous medium in a bioreactor; said aqueous medium comprising one or more microorganism; said method comprising measuring total hydrogen uptake; supplying said gaseous substrate at a flow-rate such that molar ratio of said total hydrogen uptake to supplied amount of said gaseous substrate comprises a preselected range of about 0.001 to about 1.0; further comprising adding continuous flow of aqueous medium into bioreactor; removing a continuous flow of fermentation broth from the bioreactor.

The present disclosure provides a continuous method of producing an alcohol product mixture comprising: adding gaseous substrate comprising carbon monoxide into an aqueous medium in a bioreactor; said aqueous medium comprising one or more microorganism; said method comprising measuring total hydrogen uptake; supplying said gaseous substrate at a flow-rate such that molar ratio of said total hydrogen uptake to supplied amount of said gaseous substrate comprises a preselected range of about 0.001 to about 1.0; further comprising: measuring cell density; adjusting input of gaseous substrate to increase cell density; changing specific CO uptake in predetermined amounts in a range of about 0.001 to about 10.0 mmol/min/gram dry cell; further comprising adding continuous flow of aqueous medium into bioreactor; removing a continuous flow of fermentation broth from the bioreactor.

The present disclosure provides a continuous method of producing an alcohol product mixture comprising: adding gaseous substrate comprising carbon monoxide into an aqueous medium in a bioreactor; said aqueous medium comprising one or more microorganism; measuring total hydrogen uptake and supplying said gaseous substrate comprising hydrogen at a flow-rate such that molar ratio of said total hydrogen uptake to supplied amount of said hydrogen in said gaseous substrate maintained at preselected range; further comprising adding continuous flow of aqueous medium into bioreactor; removing a continuous flow of fermentation broth from the bioreactor.

The present disclosure provides a continuous method of producing an alcohol product mixture comprising: adding gaseous substrate comprising carbon monoxide into an aqueous medium in a bioreactor; said aqueous medium comprising one or more microorganism; measuring cell mass and specific hydrogen uptake and supplying said gaseous substrate comprising hydrogen at a flow-rate such that molar ratio of said specific hydrogen uptake to supplied amount of said gaseous substrate per unit cell mass maintained at preselected range; further comprising adding continuous flow of aqueous medium into bioreactor; removing a continuous flow of fermentation broth from the bioreactor.

The present disclosure provides a continuous method of producing an alcohol product mixture comprising: adding gaseous substrate comprising carbon monoxide into an aqueous medium in a bioreactor; said aqueous medium comprising one or more microorganism; measuring cell mass and specific hydrogen uptake and supplying said gaseous substrate comprising hydrogen at a flow-rate such that molar ratio of said specific hydrogen uptake to supplied amount of said hydrogen in said gaseous substrate per unit cell mass maintained at preselected range; further comprising adding continuous flow of aqueous medium into bioreactor; removing a continuous flow of fermentation broth from the bioreactor.

As embodiments of the present disclosure: said microorganism comprises one or more of biologically pure anaerobic acetogenic bacteria; wherein said microorganism comprises one or more of naturally occurring anaerobic acetogenic bacteria; wherein said microorganism comprises one or more of non-naturally occurring anaerobic acetogenic bacteria; wherein said microorganism comprises one or more of non-naturally occurring anaerobic acetogenic bacteria produced by genetic modification using anaerobic acetogenic bacteria as host organism; wherein said microorganism comprises one or more of non-naturally occurring anaerobic acetogenic bacteria produced by inserting genes of anaerobic acetogenic bacteria into a host organism; wherein said microorganism comprises one or more bacteria selected from *Acetogenium kivui*, *Acetobacterium woodii*, *Acetoanaerobium noterae*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium autoethanogenum* (DSM 23693), *Clostridium autoethanogenum* (DSM 19630 of DSMZ Germany), *Clostridium autoethanogenum* (DSM 10061 of DSMZ Germany), *Clostridium thermoaceticum*, *Eubacterium limosum*, *Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium ultunense*, *Clostridium ragsdali* P11 (ATCC BAA-622), *Alkalibaculum bacchi* CP11 (ATCC BAA-1772), *Clostridium coskatii*, *Clostridium carboxidivorans* P7 (ATCC PTA-7827), *Geobacter sulfurreducens*, *Morrella thermacetica*, *Peptostreptococcus productus*, *Clostridium drakei*, recombinant microorganism (DSM 24138), and mixtures thereof; wherein said microorganism comprises one or more strains of *Clostridium ljundahlii*, or one or more strains of *Clostridium ragsdalei*, or one or more strains of *Clostridium carboxidivorans*, or one or more strains of *Clostridium autoethanogenum*; wherein said microorganism comprises one or more genetically modified microorganism produced by inserting one or more selected genes into host organism selected from any *Clostridium ljundahlii* strains, or any *Clostridium ragsdalei* strains, or any *Clostridium carboxidivorans* strains, or any *Clostridium autoethanogenum* strains; wherein said microorganism comprises one or more genetically modified microorganism produced by inserting into any host organism one or more genes from any *Clostridium ljundahlii* strain, or any *Clostridium ragsdalei* strain, or any *Clostridium carboxidivorans* strain, or any *Clostridium autoethanogenum* strain.

As embodiments of the present disclosure: said bioreactor comprises one or more reactor; wherein said bioreactor comprises cell recycle unit.

As an embodiment of the present disclosure, said CO-containing substrate comprises hydrogen.

As an embodiment of the present disclosure, the method comprises adding nutrient medium to said bioreactor.

Figure 1:
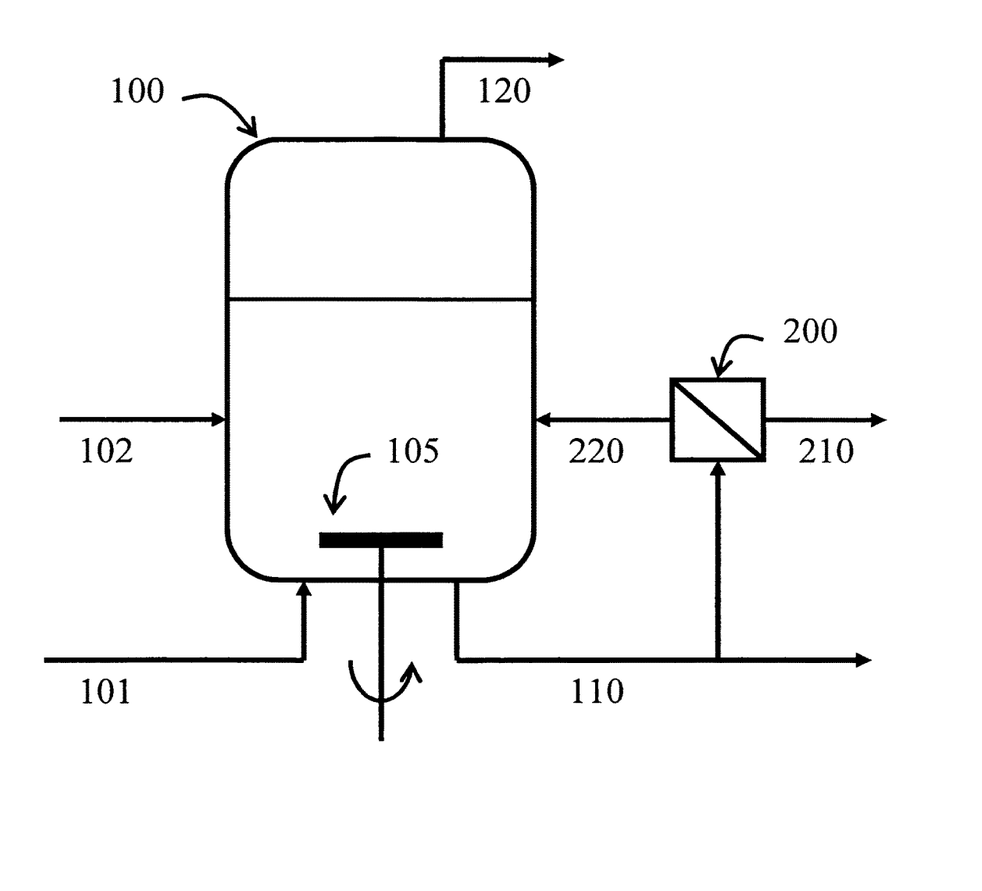
FIG. 1 comprises a schematic diagram illustrating an embodiment of the process of microbial fermentation of a gaseous substrate.

FIG. 1 presents a process for the production of chemical such as alcohol product mixture from a gaseous substrate comprising carbon monoxide (CO) such as syngas by fermentation with microorganism wherein the process comprises a bioreactor (100) containing fermentation broth comprising said microorganism cells and a fermentation medium. A gaseous stream comprising gaseous substrate comprising CO (101) can be fed into the bioreactor along with a stream of fermentation medium (102). A stream of fermentation broth (110) comprising said microorganism cells and said product chemical(s) can be removed from said bioreactor. A stream of fermentor off-gas (120) comprising unused portion of said gaseous stream comprising gaseous substrate is vented from the bioreactor. In one embodiment the stream of fermentor broth (110) flows to a cell recycle apparatus (200) wherein the cells are concentrated and returned (220) to the bioreactor. A permeate stream (210) from said cell recycle apparatus is directed to process of recovery of said chemical(s) (not shown on diagram). In one embodiment the stream of fermentor broth (110) is directed to process of recovery of said alcohol product mixture (not shown on diagram).

In one embodiment, the bioreactor (100) is equipped with an agitator (105) to provide agitation in order to facilitate contact of gaseous stream comprising gaseous substrate and enhance mass transfer of gaseous substrate with liquid fermentation medium. It is desirable to have good mass transfer rate and thus adequate agitation in the bioreactor throughout the fermentation process.

There are arrangements for collecting samples of gaseous stream comprising gaseous substrate introduced into bioreactor (101) and off-gas leaving bioreactor (120) (not shown in FIG. 1). There is arrangement for collecting samples of fermentation broth of bioreactor (not shown in FIG. 1). Said gas and liquid samples are collected at intervals and analyzed for consumption or production of various gas components, production of various products and the optical density of the fermentation broth.

These measured values can be used to calculate hydrogen uptake, specific hydrogen uptake and specific carbon monoxide (CO) uptake (SCU) and cell density in fermentation broth in the bioreactor using following equations:

$$\text{CO uptake, mmol/min} = (\text{mmol/min CO input}) - (\text{mmol/min CO output}) \quad (1)$$

$$\text{H}_2 \text{ uptake, mmol/min} = (\text{mmol/min H}_2 \text{ input}) - (\text{mmol/min H}_2 \text{ output}) \quad (2)$$

$$\text{Cell density, g/L} = (\text{Optical density}) \cdot (\text{Dilution factor}) \cdot (\text{Cell mass constant}) \quad (3)$$

$$\text{Cell mass, g} = (\text{Cell density}) \cdot (\text{Volume of bioreactor}) \quad (4)$$

$$\text{Specific CO uptake, mmol/min/g} = (\text{CO uptake})/(\text{Cell mass}) \quad (5)$$

$$\text{Specific H}_2 \text{ uptake, mmol/min/g} = (\text{H}_2 \text{ uptake})/(\text{Cell mass}) \quad (6)$$

Cell density is mass of cell per unit volume of fermentor broth. Volume of bioreactor is liquid volume in the bioreactor when agitation is turned off. Cell mass constant is mass (g) of dry microorganism cells per liter fermentation broth with optical density of one (1). Optical density (OD) is measure of amount of light absorbed by a suspension of microorganism cells in a colorimeter or spectrophotometer. The values can be used to measure turbidity, which in turn can be used to estimate the mass or number of microorganism cells in a solution or fermentation broth. Optical density of a sample is often measured after dilution of fermentor broth with a suitable solvent such as saline.

Microorganism used in the method of this disclosure may comprise one or more of biologically pure anaerobic acetogenic bacteria.

Microorganism used in the method of this disclosure may comprise one or more of naturally occurring anaerobic acetogenic bacteria.

Microorganism used in the method of this disclosure may comprise one or more of non-naturally occurring anaerobic acetogenic bacteria.

Microorganism used in the method of this disclosure may comprise one or more of non-naturally occurring anaerobic acetogenic bacteria produced by genetic modification using anaerobic acetogenic bacteria as host organism.

Microorganism used in the method of this disclosure may comprise one or more of non-naturally occurring anaerobic acetogenic bacteria produced by inserting genes of anaerobic acetogenic bacteria into a host organism.

Microorganism used in the method of this disclosure may comprise one or more microorganism selected from *Acetogenium kivui*, *Acetobacterium woodii*, *Acetoanaerobium noterae*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium autoethanogenum* (DSM 23693), *Clostridium autoethanogenum* (DSM 19630 of DSMZ Germany), *Clostridium autoethanogenum* (DSM 10061 of DSMZ Germany), *Clostridium thermoaceticum*, *Eubacterium limosum*, *Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium ultunense*, *Clostridium ragsdali* P11 (ATCC BAA-622), *Alkalibaculum bacchi* CP11 (ATCC BAA-1772), *Clostridium coskatii*, *Clostridium carboxidivorans* P7 (ATCC PTA-7827), *Geobacter sulfurreducens*, *Morrella thermacetica*, *Peptostreptococcus productus*, *Clostridium drakei*, recombinant microorganism (DSM 24138), and mixtures thereof.

In one embodiment, microorganism used in the method of this disclosure comprises one or more strains of *Clostridium ljungdahlii*, or one or more strains of *Clostridium ragsdalei*, or one or more strains of *Clostridium carboxidivorans*, or one or more strains of *Clostridium autoethanogenum*.

In one embodiment, microorganism used in the method of this disclosure comprises one or more genetically modified micro-organism produced by inserting one or more selected genes into host organism selected from any *Clostridium ljungdahlii* strains, or any *Clostridium ragsdalei* strains, or any *Clostridium carboxidivorans* strains, or any *Clostridium autoethanogenum* strains.

In one embodiment, microorganism used in the method of this disclosure comprises one or more genetically modified micro-organism produced by inserting into any host organism one or more genes from any *Clostridium ljungdahlii* strain, or any *Clostridium ragsdalei* strain, or any *Clostridium carboxidivorans* strain, or any *Clostridium autoethanogenum* strain.

In the method of the present disclosure, specific hydrogen uptake is decreased gradually to a desirable specific hydrogen uptake.

In one embodiment of the present disclosure the method comprises measuring total hydrogen uptake and supplying said gaseous substrate comprising hydrogen at a flow-rate such that molar ratio of said total hydrogen uptake to supplied amount of said gaseous substrate comprising hydrogen is maintained in a preselected range.

In one embodiment said preselected range of value of molar ratio of said total hydrogen uptake to supplied amount of said gaseous substrate comprising hydrogen comprises a range of about 0.1% to about 1.0%.

In one embodiment the method further comprises supplying a flow of fermentation medium.

In one embodiment the method further comprises using cell recycle with a permeate removal in a specified range of value.

In one embodiment said gaseous substrate comprising hydrogen also comprises CO. In one embodiment the method further comprises measuring cell density and specific CO uptake and increasing cell density by adjusting input of gaseous substrate; wherein specific CO uptake is increased or decreased in steps of predetermined value.

In one embodiment the method further comprises a sub-process of measuring cell density and specific CO uptake and if cell density is less than a target cell density, selecting a target specific CO uptake and adjusting flow of gaseous stream comprising gaseous substrate such that specific CO uptake is equal to said target specific CO uptake can be attained.

In one embodiment said sub-process is repeated until a desired cell density is attained or a desired specific CO uptake is attained or desired ethanol productivity is attained or desired ethanol concentration in the fermentation broth is attained.

One embodiment of the method of the present disclosure comprises measuring total hydrogen uptake and supplying said gaseous substrate comprising hydrogen at a flow-rate such that molar ratio of said total hydrogen uptake to supplied amount of said hydrogen in said gaseous substrate comprising hydrogen is maintained in a preselected range.

One embodiment of the method of the present disclosure comprises measuring microorganism cell mass and specific hydrogen uptake and supplying said gaseous substrate comprising hydrogen at a flow-rate such that molar ratio of said specific hydrogen uptake to supplied amount of said gaseous substrate comprising hydrogen per unit microorganism cell mass is maintained in a preselected range.

One embodiment of the method of the present disclosure comprises measuring microorganism cell mass and specific hydrogen uptake and supplying said gaseous substrate comprising hydrogen at a flow-rate such that molar ratio of said specific hydrogen uptake to supplied amount of said hydrogen in said gaseous substrate comprising hydrogen per unit microorganism cell mass is maintained in a preselected range.

Said preselected range of value of molar ratio of said total hydrogen uptake to supplied amount of said hydrogen in said gaseous substrate comprising hydrogen comprises a range of about 0.1% to about 1.0%.

Said preselected range of value of molar ratio of said specific hydrogen uptake to supplied amount of said gaseous substrate comprising hydrogen per unit microorganism cell mass comprises a range of about 0.1% to about 1.0%.

Said preselected range of value of molar ratio of said specific hydrogen uptake to supplied amount of said hydrogen in said gaseous substrate comprising hydrogen per unit microorganism cell mass comprises a range of about 0.1% to about 1.0%.

Value of said target specific CO uptake may comprise a range of about 0.1 to about 10.0 mmol CO per minute per gram dry microorganism. Value of said desired specific CO uptake may comprise a range of about 0.1 to about 10 mmol/min/g.

Value of said target cell density may comprise a range of about 0.1 to about 50 g/L. Value of said desired cell density may comprise a range of 0.5 to 50 g/L.

Value of said desired ethanol productivity comprises a range of 1 to 50 g/L/day.

Value of said desired ethanol concentration in the fermentation broth comprises a range of 1 to 20 g/L.

Typically in a laboratory scale bioreactor such as New Brunswick Bioflow I bioreactor, agitator speed in the range of 300-900 revolutions per minute (rpm) provides adequate agitation for desirable mass transfer rate. In one embodiment, agitator speed in the range of 500-700 rpm is used. In one embodiment, agitator speed in the range of 550-650 rpm is used. In one embodiment, agitator speed of about 600 rpm is used.

In an embodiment, for a larger scale bioreactor such as a bioreactor of about 100 to 500 liter size, agitator speed in the range of about 50 to about 500 rpm is used for agitation. In an embodiment, for a commercial scale bioreactor of about 100,000 to about 1000,000 liter size, agitator speed in the range of about 1 to about 50 rpm is used for agitation. In various embodiments, a larger bioreactor requires smaller rpm compared to a smaller bioreactor.

As an embodiment, the present disclosure provides temperature control in the bioreactor in the range of 25 to 50° C.

In one embodiment of the method of the present disclosure, said bioreactor comprises one reactor. In one embodiment of the method of the present disclosure, said bioreactor comprises two or more reactors.

In one embodiment of the method of the present disclosure, said bioreactor comprises cell recycle unit.

In one embodiment, the hydrogen uptake to rate of input of gaseous substrate changes to maintain optimal growth. As further embodiments, CO and $H_2$ composition comprises 38% and 25%, respectively, in the input gas desired targeted molar ratio of $H_2$ uptake to total gas molecule input comprises 11 to 14 (e.g. first preselected range); wherein CO and $H_2$ composition comprises 30% and 15%, respectively, in the input gas desired targeted molar ratio of $H_2$ uptake to total gas molecule input comprises 3 to 4.5 (e.g. second preselected range).

In one embodiment of the method of the present disclosure, said gaseous stream comprising gaseous substrate comprising CO also comprises hydrogen. In one embodiment, said gaseous stream comprising gaseous substrate comprising CO comprises syngas. In one embodiment, said gaseous stream comprising gaseous substrate comprising CO comprises steel mill off-gas. In one embodiment, said gaseous stream comprising gaseous substrate comprising CO comprises syngas obtained by gasification of carbonaceous material comprising biomass.

In one embodiment one or more growth or seed fermentors provide the initial supply of inoculum of microorganism cells. In one embodiment one or more growth or seed fermentors continue to supply microorganism cells to bioreactor in conjunction with the method of this disclosure. In one embodiment of the present disclosure, the process comprises cell recycle.

Nutrient medium comprises microorganism growth medium which may contain one or more of vitamins and minerals that permit growth of selected microorganism. Table 1 provides an embodiment of nutrient medium as contemplated by the present disclosure. Other nutrient medium suitable for the present disclosure is known in the art. Moreover, nutrient medium that is not disclosed in the art but derived from various components described in Table 1 can be utilized by the present invention. The present disclosure provides for improved compositions of nutrient medium.

TABLE 1

Medium Component and Their Concentrations

| Component/Ion | Added As | Conc in ppm |
|---|---|---|
| $NH_4^+$ | $NH_4Cl/(NH_4)_2HPO_4$ | ≤838 |
| Fe | $FeCl_2 \cdot 4H_2O$ | ≤17 |
| Ni | $NiCl_2 \cdot 6H_2O$ | ≤0.2 |
| Co | $CoCl_2 \cdot 6H_2O$ | ≤1.0 |
| Se | $Na_2SeO_3$ | ≤0.1 |
| Zn | $ZnSO_4 \cdot 7H_2O$ | ≤0.5 |
| Mo | $Na_2MoO_4 \cdot 2H_2O$ | ≤0.3 |
| Mn | $MnCl_2 \cdot 4H_2O$ | ≤0.2 |
| B | $H_3BO_3$ | ≤1.1 |
| Cu | $CuCl_2 \cdot 2H_2O$ | ≤0.15 |
| W | $Na_2WO_4 \cdot 2H_2O$ | ≤1.2 |
| K | KCl | ≤79 |
| Mg | $MgCl_2 \cdot 6H_2O$ | ≤60 |
| Na | NaCl | ≤80* |
| Ca | $CaCl_2 \cdot 2H_2O$ | ≤55 |
| Cysteine HCl | Cysteine HCl | ≤250 |
| $PO_4^{-2}$ | $H_3PO_4/(NH_4)_2HPO_4$ | ≤820 |
| Pantothenic Acid | Pantothenic Acid | ≤0.04 |
| Biotin | Biotin | ≤0.02 |
| Thiamin | Thiamine | ≤0.05 |

*$Na^+$ concentration is from NaCl only. It does not include $Na^+$ from the other components such as $Na_2WO_4 \cdot 2H_2O$.
**$Ca^{+2}$ concentration does not include calcium from pantothenic acid, calcium salt (i.e. Calcium d-Pantothenate).

EXAMPLES

Comparative Example (Example 11 in U.S. Pat. No. 7,285,402)

To prepare the stock cultures for inoculation of the reactor, cultures of *Clostridium ljungdahlii*, strain C-01 (ATCC Accession No. 55988) were grown up in 150 mL serum bottles on CO, $CO_2$ and $H_2$ in a rich medium containing 1 g/L yeast extract and 1 g/L trypticase, in salts and vitamins. The vitamin concentration employed was 0.4 mL/L medium of an aqueous solution containing 50.5 mg/L calcium pantothenate, 20.6 mg/L d-biotin and 50.6 mg/L thiamine HCl. Bottles were incubated at 37° C. in a shaker incubator. The cultures were grown to the exponential growth phase, as determined by visual inspection. With each inoculation, approximately 90 mL of stock culture were transferred from serum bottles to 1 liter of medium, representing 9% by volume inoculation. A successful inoculation is described below. The outlined procedure can be repeated several times to obtain a successful inoculation.

In obtaining a successful inoculation, 90 mL/L of inoculum were added to a 1 liter batch of basal medium containing 0.4 mL/L vitamins and salts (t=0). The agitation rate was 240 rpm, the pH was 5.3, the temperature was 38.5° C. and the gas retention time (continuous gas flow) was 110 minutes. The gas feed contained 62% $H_2$, 31% CO and 7% $C_2H_6$. After 13 hr (t=13 hr) some CO conversion was noted, and at t=23 hr the agitation rate was increased from 240 rpm to 300 rpm. The gas retention time was decreased to 100 minutes at t=27 hr, and a further decrease in gas retention time was made at t=46 hr. The agitation rate was also increased in 100 rpm increments at t=28 hr, 59 hr, 72 hr and 85 hr.

By t=110 hr, the system was operating with a gas retention time of 80 minutes and an agitation rate of 600 rpm. The cell concentration was 0.5 g/L and the CO conversion was 35%. There was still no $H_2$ conversion, but small amounts of ethanol and acetate (about 1 g/L each) had accumulated in the batch culture broth. The efforts up until this time emphasized cell growth in the reactor.

Medium flow using the same concentrations as in basal medium was started at a rate of 0.4 ml/min at t=120 hr. A program of nominal increases in gas rate, agitation rate and medium rate was then initiated while carefully maintaining the system under excess $H_2$. By t=210 hr, the ethanol concentration was 17 g/L, the acetate concentration was 1 g/L, the cell concentration was 1.6 g/L, the CO conversion was nearly 100% and the $H_2$ conversion was 90%. The ethanol productivity reached 11.4 g/L-day.

A program of gradual gas rate increases was again started. Concurrent vitamin increases were made to bring the vitamin addition rate to 0.7 ml/L medium. By t=610 hr, the reactor was producing 20 g/L ethanol and about 2 g/L acetate. The CO conversion was nearly 100% and the $H_2$ conversion was 85%. The ethanol productivity reached 14 g/L/day.

Fermentation Medium for examples 1-7 comprise one or more components selected from those presented in Table 1.

Example 1: *Clostridium ljungdahlii* PETC: Increasing the Density of Bacteria in the Reactor by Maintaining the Percentage of Uptake of Hydrogen at 4.5% of Total Gas Flowing into the Reactor New Brunswick bioflow I reactor containing Fermentation Medium was started with 0.34 g/L of actively growing *Clostridium ljungdahlii* PETC strain. The rate of agitation of the reactor was set to 500 rpm at the start of the experiment. This agitation rate was maintained throughout the experiment. Temperature in the bioreactor was maintained in the range of about 38 to about 39° C. throughout the experiment. Samples of syngas feed into the bioreactor and off-gas from the bioreactor and fermentation broth in the bioreactor were taken at intervals (e.g. 1 interval) and were analyzed for consumption or production of various gas components, broth acetic acid concentration, broth ethanol concentration and the optical density of the culture.

Molar ratio of total $H_2$ uptake to syngas input was set at 4.5%. Required syngas flow corresponding to this above molar ratio (4.5%) was calculated using the equations (1)-(6). The bioreactor was supplied with syngas at the rate calculated above.

In this example, to increase the stability of the culture maximum gas increase at any given time point was limited to 30% of the current gas flow value. Also gas was not increased if the culture was not utilizing 70% of the CO provided to the reactor at any given point.

A cell recycle system (CRS) was attached to the reactor 21 hours after the inoculation.

After the attachment of cell recycle system media (nutrient) flow to the reactor was started at a rate of 1.1 ml/min and through the cell recycle system 1 ml/min permeate was drawn out from the reactor.

The above modification to the reactor was carried out to prevent accumulation of inhibitory amounts of acetic acid and ethanol in the culture and also to provide adequate amounts of nutrients to the culture. Cell mass increased with time and reached the cell mass of 3.2 g/L within 46 hours after the inoculation of the reactor. At this point culture was producing 6.9 g/L of ethanol and 4.86 g/L acetic acid.

In this particular experiment pH of the culture was maintained between 4.78 and 5.00 through out the experiment.

After bacteria started growing actively in the reactor (when the cell density of the reactor reach about 50% more than the initial cell density) culture was supplemented with composition of vitamins (in addition to the vitamins already in the medium) if the acetic acid concentration of the culture broth is below a predetermined value. Criteria used to add cocktail of vitamins to the culture was as follow as: if the culture broth acetic acid is less than about 2.5 g/L, about 0.34 mL of vitamins per liter of culture was added, if the culture broth acetic acid is less than about 2 g/L, about 0.67 mL of vitamins per liter of culture was added, if the culture broth acetic acid is less than about 1.5 g/L, about 1 mL of vitamins per liter was added. Composition of vitamins used in these experiments were as follows:

| | |
|---|---|
| Biotin | 0.08-1 µM |
| Thiamin HCl | 0.12-1.5 µM |
| Calcium d-pantothenate | 0.15-2 µM |

ATCC vitamin supplement (catalog No. MD-VS) was added to PETC example to the final concentration of 1% (of fermentation medium) in addition to the Biotin, Thiamin and calcium pantothenate.

Example 2: *Clostridium ljungdahlii* C-01: Increasing the Density of Microorganism in the Reactor by Maintaining the Percentage of Uptake of Hydrogen at about 3% of Total Gas Flowing into the Reactor New Brunswick Bioflow I bioreactor containing about 1.5 liter (e.g. in the range of about 1.45 to about 1.6 liters) of fermentation medium was started with about 0.38 g/L of actively growing *Clostridium ljungdahlii* C-01 strain. Before the start of the experiment the rate of agitation in the bioreactor was set to 600 rpm. This agitation rate was maintained throughout the experiment. Temperature in the bioreactor was maintained in the range of about 36 to about 37.5° C. throughout the experiment. Samples of syngas feed into the bioreactor and off-gas from the bioreactor and fermentation broth in the bioreactor were taken at intervals (e.g. 1 hour interval) and were analyzed for consumption or production of various gas components, broth acetic acid concentration, broth ethanol concentration and the optical density of the culture.

Molar ratio of total $H_2$ uptake to syngas input was set at about 3%. Required syngas flow corresponding to this above molar ratio (3%) was calculated using the equations (1)-(6). The bioreactor was supplied with syngas at the rate calculated above. About 12 hours after the inoculation, a flow of fermentation medium to the bioreactor was started at a rate of 0.1 mL/min (approximate cell retention time: 250 hours). After about 32 hours after the inoculation, rate flow of fermentation medium to the bioreactor was increased to 0.3 mL/min (approximate cell retention time 75 hours). After about 47 hours after the inoculation, cell recycle system ("crs" or "CRS") was attached to the reactor when the broth ethanol concentration of the reactor reached 9.4 g/L. After the attachment of CRS to the reactor Fermentation Medium flow was increased from 0.3 to 0.8 and flow of 0.5 mL/min cell free permeate was drawn out from the reactor through the CRS. With this amount of permeate extraction culture was maintain under 12 g/L ethanol until 56 hours after the inoculation.

Cell mass increased with time and reached 2.8 g/L of cells within about 56 hours after inoculation of the bioreactor.

Example 3: *Clostridium ljungdahlii* C-01: Increasing the Density of Microorganism in the Reactor by Maintaining the Percentage of Uptake of Hydrogen at 4.5% of Total Gas Flowing into the Reactor New Brunswick Bioflow I reactor containing about 1.5 liter (e.g. in the range of 1.5 to 1.675 liters) of fermentation medium was started with 0.37 g/L of actively growing *Clostridium ljungdahlii* C-01 strain. Before the start of the experiment rate of agitation in the bioreactor was set to 600 rpm. This agitation rate was maintained throughout the experiment. Temperature in the bioreactor was maintained in the range of about 36 to about 37.5° C. throughout the experiment. Samples of syngas feed into the bioreactor and off-gas from the bioreactor and fermentation broth in the bioreactor were taken at intervals (e.g. 1 interval) and were analyzed for consumption or production of various gas components, broth acetic acid concentration, broth ethanol concentration and the optical density of the culture.

Molar ratio of total $H_2$ uptake to syngas input was set at 4.5%. Required syngas flow corresponding to this above molar ratio (4.5%) was calculated using the equations (1)-(6). The bioreactor was supplied with syngas at the rate calculated above. At 13 hours after the inoculation media flow to the reactor was started at 0.1 ml/min (approximate cell retention time: 250 hours). At 47.5 hours after the inoculation the media flow to the reactor was increased to 0.23 ml/min (approximate cell retention time 116 hours). At 71.42 hours after the inoculation the media flow to the reactor was increased to 0.315 ml/min (approximate cell retention time 85 hours). In this particular example a cell recycle system was not attached to the reactor.

Cell mass increased with time and reached 2.75 g/L within 99 hours after inoculation of the bioreactor. At this point culture was producing 11.6 g/L/day of ethanol.

Example 4: *Clostridium autoethanogenum*

New Brunswick bioflow I reactor containing Fermentation Medium was started with 0.46 g/l of actively growing *Clostridium autoethanogenum*. The rate of agitation of the reactor was set to 600 rpm at the start of the experiment. This agitation rate was maintained throughout the experiment. Temperature in the bioreactor was maintained in the range of about 36 to about 37.5° C. throughout the experiment. Samples of syngas feed into the bioreactor and off-gas from the bioreactor and fermentation broth in the bioreactor were taken at intervals (e.g. 1 interval) and were analyzed for consumption or production of various gas components, broth acetic acid concentration, broth ethanol concentration and the optical density of the culture.

Molar ratio of total $H_2$ uptake to syngas input was set at 4.5%. Required syngas flow corresponding to this above molar ratio (4.5%) was calculated using the equations (1)-(6). The bioreactor was supplied with syngas at the rate calculated above.

In this example, to increase the stability of the culture gas was not increased if the culture was not utilizing 80% of the CO provided to the reactor at any given point.

At 8.37 hours after the inoculation media flow to the reactor was started at 0.1 ml/min (approximate cell retention time: 233 hours). At 20.40 hours after the inoculation the media flow to the reactor was increased to 0.21 ml/min (approximate cell retention time 109 hours). At 42.15 hours after the inoculation the media flow to the reactor was increased to 0.32 ml/min (approximate cell retention time 75.5 hours).

At 43.75 hours after the inoculation cell recycle system (CRS) was attached to the reactor when the broth ethanol concentration of the reactor reached 12.5 g/L. After the attachment of CRS media flow to the reactor was increased to 0.6 ml/min and through the CRS 0.3 ml/min permeate was drawn out from the reactor (approximate cell retention time 80.5 hours). With this amount of permeate extraction culture was maintain under 19 g/L ethanol until 57 hours after the inoculation. This modification (introduction of CRS) was done to the system to remove rapid build up of ethanol in the reactor.

As shown in the FIG. 1 cell mass increased with time and reached the cell mass of 3.7 g/L within 58 hours after the inoculation of the reactor. At this point culture was producing more 18.4 g/L of ethanol.

Example 5: *Clostridium ljungdahlii* C-01

New Brunswick Bioflow I bioreactor containing about 1.5 liter (e.g. in the range of 1.45 to 1.65 liters) of Fermentation Medium was started with about 0.3 g/L of actively growing *Clostridium ljungdahlii* C-01 strain. At the start of the experiment, the rate of agitation in the bioreactor was set to 600 rpm. This agitation rate was maintained throughout the experiment. Temperature in the bioreactor was maintained in the range of about 36 to about 37.5° C. throughout the experiment. Samples of the following were taken and analyzed at different intervals (e.g. 1 to 4 hour interval): syngas feed into the bioreactor; off-gas from the bioreactor; fermentation broth in the bioreactor. The sample analysis provided: consumption of various gaseous components, production of various gaseous components, concentration of acetic acid, concentration of ethanol and optical density of the fermentation broth.

Thus Specific CO uptake (SCU) was determined using equations (1)-(6) described above.

Initially, a value of syngas input was calculated using above equations corresponding to SCU value of about 1.4 mmol/min/g and flow of syngas was maintained at this calculated value until cell density increased and reached a value of about 1.5 g/L.

Once the cell density of the reactor reached about 1.5 g/L the set SCU value to predict gas was lowered to about 1.2 mmol/min/g. Thereafter once the cell mass of the reactor reached about 2.5 g/L the set SCU value to predict gas was lowered to about 1.0 mmol/min/g. Cell mass increased with time and reached the expected cell mass of about 2.8 g/L within about 79 hours after the inoculation of the reactor. At this point culture was producing more than about 20 g/L of ethanol.

About 13.97 hours after the inoculation media flow to the reactor was started at about 0.2 ml/min (approximate cell retention time: about 125 hours). About 28.08 hours after the inoculation media flow to the reactor was increased to about 0.5 ml/min (approximate cell retention time: about 52 hours). During the experiment pH was maintained around about 4.5.

The gradual lowering of the set SCU through out the start-up procedure is to facilitate the gradual transformation of the culture to low SCU (between about 0.7 to about 0.9 mmol/min/g) maintain during the production mode (steady state) of the reactor.

Above mention process takes less than about 80 hours to reach the set goal of cell mass (about 2.8 g/L) of the reactor.

Example 6: *Clostridium autoethanogenum*

New Brunswick Bioflow I bioreactor containing about 1.5 liter (e.g. in the range of about 1.45 to about 1.65 liters) of Fermentation Medium was started with about 0.47 g/L of actively growing *Clostridium autoethanogenum*. At the start of the experiment, the rate of agitation in the bioreactor was set to about 600 rpm. This agitation rate was maintained throughout the experiment. Temperature in the bioreactor was maintained in the range of about 36 to about 37.5° C. throughout the experiment. Samples of the following were taken and analyzed at different intervals (e.g. about 1 to about 4 hour interval): syngas feed into the bioreactor; off-gas from the bioreactor; fermentation broth in the bioreactor. The sample analysis provided: consumption of various gaseous components, production of various gaseous components, concentration of acetic acid, concentration of ethanol and optical density of the fermentation broth.

Thus specific CO uptake (SCU) was determined using equations (1)-(6) described above.

Initially, a value of syngas input was calculated using above equations corresponding to SCU value of about 0.4 mmol/min/g and flow of syngas was maintained at this calculated value until cell density increased. Gas flow corresponding to target SCU value of about 0.4 mmol/min/g was maintained for about 19 hours. Between the period of 19 and 21 hours after the inoculation targeted SCU value was about 0.5 mmol/min/g. Targeted SCU value was set to about 0.6 at about 21 hours after the inoculation. Cell density increased with time and reached about 3 g/L within about 79 hours after the inoculation of the reactor. At this point culture was producing more than about 15 g/L of ethanol. About 26 hours after the inoculation media flow to the reactor was started at about 0.1 ml/min (approximate cell retention time: about 240 hours). About 50 hours after the inoculation media flow to the reactor was increased to about 0.2 ml/min (approximate cell retention time: about 119 hours). About 71 hours after the inoculation media flow to the reactor was increased to about 0.5 ml/min (approximate cell retention time: about 50 hours). During the experiment pH was maintained around about 4.5.

Example 7: *Butyribacterium methylotrophicum* (ATCC 33266): Increasing the Density of Bacteria in the Reactor by Maintaining the Percentage of Uptake of Hydrogen at 4.5% of Total Gas Flowing into the Reactor In this experiment $H_2$ uptake start-up method was tested with a well studied non-clostridial acetogen.

This experiment was started in a New Brunswick bioflow I reactor containing 0.78 g/L of actively growing *Butyribacterium methylotrophicum* in the previously mentioned fermentation medium. The rate of agitation of the reactor was set to 700 rpm at the start of the experiment. This agitation rate was maintained throughout the experiment. Temperature in the bioreactor was maintained in the range of about 38 to about 38.6° C. throughout the experiment. Samples of syngas feed into the bioreactor and off-gas from the bioreactor and fermentation broth in the bioreactor were taken at intervals (e.g. 1 interval) and were analyzed for consumption or production of various gas components, broth acetic acid concentration, broth ethanol concentration and the optical density of the culture.

The target molar ratio of total $H_2$ uptake to syngas input was set at 4.5%. Required syngas flow corresponding to this above molar ratio (4.5%) was calculated using the equations (1)-(6). The bioreactor was supplied with syngas at the rate calculated above.

In this example, to increase the stability of the culture maximum gas increase at any given time point was limited to 30% of the current gas flow value. Also, gas was not increased if the culture was not utilizing 80% of the CO provided to the reactor at any given point.

Growth medium (nutrient) flow to the reactor was started at a rate of 1 ml/min and through the Cell Recycle System (CRS) attached to the reactor 1 ml/min permeate was drawn out from the reactor.

Cell density of the culture increased with time and reached the cell mass of 5.12 g/L within 34 hours after the inoculation of the reactor. At this point culture was producing 10.81 g/L of ethanol and 3.96 g/L acetic acid. In this particular experiment pH of the culture was maintained between 4.67 and 5.00 throughout the experiment.

Numerous modifications and variations of the present disclosure could be made by those skilled in the art without departing from the scope of the present disclosure included in the specific embodiments, examples, claims, application, etc., thereof. All published documents are incorporated by reference herein.

We claim:

1. A process for increasing cell density in a microbial fermentation of a gaseous substrate, the process comprising:
    (a) contacting an anaerobic acetogenic bacteria in an aqueous medium with a gaseous substrate comprising hydrogen and carbon monoxide in a bioreactor, thereby forming a fermentation medium;
    (b) adjusting an amount of hydrogen provided to the fermentation medium comprising:
        (i) measuring a rate of input of hydrogen into the bioreactor;
        (ii) measuring a rate of output of hydrogen from the bioreactor;
        (iii) determining a hydrogen uptake from the measured hydrogen input and output rates;
        (iv) maintaining a hydrogen uptake in a range of about 0.001 to about 1.0 mmol/min by increasing or decreasing a rate of hydrogen input; and
        (v) maintaining a molar ratio of $H_2$ uptake to total gas molecules input to the bioreactor in a range of about 3% to about 4.5%,
    wherein the process provides a cell density in a range of about 0.5 to about 50 g/L, wherein said cell density is obtained thereby at a faster rate than by a reference process lacking the hydrogen adjusting step.

2. The process of claim 1 wherein the hydrogen uptake is maintained in a range of about 0.005 to about 0.5 mmol/min.

3. The process of claim 1 wherein the hydrogen uptake is maintained in a range of about 0.01 to about 0.1 mmol/min.

4. The process of claim 1 wherein the anaerobic acetogenic bacteria are selected from the group consisting of biologically pure microorganisms, naturally occurring microorganisms, non-naturally occurring microorganisms, non-naturally occurring microorganism produced by genetic modifications, mutants of naturally occurring microorganisms, mutants of non-naturally occurring microorganisms, recombinant microorganisms, engineered microorganisms, and artificially synthesized microorganism.

* * * * *